United States Patent [19]

Wilson et al.

[11] Patent Number: 5,196,539
[45] Date of Patent: Mar. 23, 1993

[54] ESTER-CONTAINING QUATERNARY PYRIDINIUM SALTS

[75] Inventors: John W. Wilson, Rochester; Alexandra D. Bermel, Spencerport, both of N.Y.

[73] Assignee: Eastman Kodak Company, Rochester, N.Y.

[21] Appl. No.: 734,355

[22] Filed: Jul. 18, 1991

[51] Int. Cl.$^5$ .................................... C07D 213/55
[52] U.S. Cl. .................................... 546/301; 546/341; 546/342
[58] Field of Search .................. 546/301, 341, 342

[56] References Cited

PUBLICATIONS

Porai-Koshits, et al. *Zh. Prikl. Khim.* 37(5) (1964), pp. 1081–1087.
Clausen et al. *J. Med. Chemistry* (1979) vol. 22(2) pp. 177–180. Synthesis of Pyridinium Analogues of Acetycholine and Their Interactions with Intestinal Muscarinic Receptors.
Katritzky et al. *J. Chem. Res. Miniprint* (1978) pp. 4783–4797. The Reactions of Pyrylium Salts with Aliphatic Diamines and Chloro- and Hydroxy-amines.

*Primary Examiner*—C. Warren Ivy
*Assistant Examiner*—P. G. Spivack
*Attorney, Agent, or Firm*—Willard G. Montgomery

[57] ABSTRACT

New ester-containing quaternary pyridinium salts are provided having advantageous utility as charge control agents in electrostatographic toners and developers. The salts have the structure:

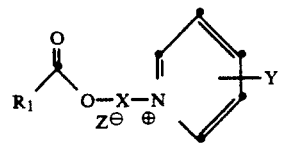

wherein $R_1$ is alkyl or aryl, X is $+CH_2+_n$, Y is hydrogen, alkyl, alkoxy or halogen, $Z^\ominus$ is an anion and n is an integer from 2 to 6.

Such ester-containing quaternary pyridinium salts also cause toner particles containing them to display lower fusing temperature and improved paper adhesion indexes.

9 Claims, No Drawings

ESTER-CONTAINING QUATERNARY PYRIDINIUM SALTS

FIELD OF THE INVENTION

This invention relates to certain new estercontaining quaternary pyridinium salts which are useful as charge control agents in dry electrostatographic toners and developers that also serve as adhesion promoters between toner and receiver sheets and as toner fusing temperature reducers.

BACKGROUND OF THE INVENTION

In the art of making and using toner powders, charge control agents are commonly employed to adjust and regulate the triboelectric charging capacity and/or the electrical conductivity characteristics thereof. Many different charge control agents are known which have been incorporated into various binder polymers known for use in toner powders. However, the need for new and improved toner powders that will perform in new and improved copying equipment has resulted in continuing research and development efforts to discover new and improved charge control agents.

Of potential interest are substances which not only serve as toner powder charge control agents, but also function as agents that provide additional results or effects such as promoting adhesion between toner and receiver sheets and as toner fusing temperature reducers. Such multi-functionality offers the potential for achieving cost savings in the manufacture and use of toner powders, developers and copier equipment.

It would, therefore, be desirable to provide new salts that could perform the charge-controlling function well in dry, electrostatographic toners and developers as well as promote the adhesion between toner and receiver sheets and, in addition thereto, serve as toner fusing temperature reducers.

SUMMARY OF THE INVENTION

This invention provides new ester-containing quaternary pyridinium salts having the structure:

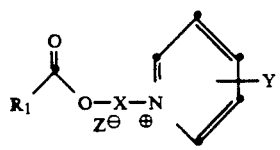

wherein $R_1$ is alkyl or aryl, X is $+CH_2+$, Y is hydrogen, alkyl, alkoxy or halogen, $Z^-$ is an anion and n is an integer from 2 to 6.

The salts of this invention have advantageous utility as charge control agents in dry, particulate electrostatographic toner powders. Such toner powders comprise a polymeric matrix phase or a polymeric binder which has dispersed therein at least one quaternary pyridinium salt having incorporated therein at least one ester-containing moiety that is bonded through an alkylene linking group to the pyridinium nitrogen atom.

When incorporated into toner powders, such quaternary pyridinium salts not only function as good charge control agents, but also serve as toner powder fusing temperature depressants and paper adhesion promoters. These salts are preferably dispersed in the polymeric binder matrix phase comprising the core or body portion of a toner particle.

Toner powders containing the novel salts of this invention can also be mixed with a carrier vehicle to form electrostatographic developers.

Toner powders containing these salts incorporated into the polymeric binder thereof can be used for producing developed toned images on a latently imaged photoconductor element, for transfer of the toned image from the photoconductor element to a receiver sheet and for heat fusion of the toned image on the receiver while employing processes and processing conditions heretofore generally known to the art of electrophotography.

Various other advantages, aims, features, purposes, embodiments and the like associated with the present invention will be apparent to those skilled in the art from the present specification taken with the accompanying claims.

DESCRIPTION OF THE PREFERRED EMBODIMENTS

(A) Definitions

The term "particle size" as used herein, or the term "size", or "sized" as employed herein in reference to the term "particles", means volume weighted diameter as measured by conventional diameter measuring devices, such as a Coulter Multisizer, sold by Coulter, Inc. Mean volume weighted diameter is the sum of the mass of each particle times the diameter of a spherical particle of equal mass and density, divided by total particle mass.

The term "glass transition temperature" or "Tg" as used herein means the temperature at which a polymer changes from a glassy state to a rubbery state. This temperature (Tg) can be measured by differential thermal analysis as disclosed in "Techniques and Methods of Polymer Evaluation", Vol. 1, Marcel Dekker, Inc., N.Y., 1966.

The term "melting temperature" or "Tm" as used herein means the temperature at which a polymer changes from a crystalline state to an amorphous state. This temperature (Tm) can be measured by differential thermal analysis as disclosed in "Techniques and Methods of Polymer Evaluation".

The term "adhesion index" as used herein is a measure of toner adhesion to paper after the toner has been fused. The adhesion index test involves adhering a metal block to a toner patch and measuring the energy required to cause interfacial failure between the toner layer and its contacting substrate by collision of a pendulum with the metal block. The range of adhesion index is from 0 units (no adhesion of the toner to the substrate) to 100 units (excellent adhesion of the toner to the substrate).

(B) Ester-Containing Quaternary Pyridinium Salts

This invention is directed to estercontaining quaternary pyridinium salts of the formula:

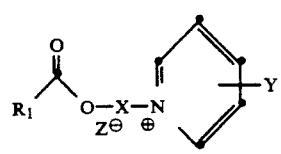

wherein $R_1$ is alkyl or aryl, X is +CH$_2$+, Y is hydrogen, alkyl, alkoxy or halogen, $Z^\ominus$ is an anion and n is an integer from 2 to 6.

As used herein, the term "alkyl" includes straight and branched chain alkyl groups and cycloalkyl groups.

As used herein, the term "anion" refers to negative ions such as m-nitrobenzenesulfonate, tosylate, tetraphenylborate, dicyanamide, chloride and the like.

As used herein, the term aryl includes phenyl, naphthyl and anthryl.

As used herein, the term "alkoxy" includes methoxy, ethoxy, propoxy and butoxy.

As used herein, the term "halogen" includes fluorine, chlorine, bromine and iodine.

Alkyl and aryl groups can be unsubstituted or substituted with a variety of substituents such as alkoxy, halo or other groups.

Illustrative examples of ester-containing quaternary pyridinium salts useful in the present invention include, for example:

N-[2-benzoyloxyethyl]pyridinium m-nitrobenzenesulfonate;

N-[2-(4-chlorobenzoyloxy)ethyl]pyridinium m-nitrobenzenesulfonate;

N-[3-(3-nitrobenzoyloxy)propyl]pyridinium tetraphenylborate;

N-[2-(2-naphthoyloxy)ethyl]pyridinium tetraphenylborate;

N-[2-acetyloxyethyl]pyridinium tetraphenylborate;

N-[2-acetyloxyethyl]pyridinium m-nitrobenzenesulfonate;

N-[4-propionyloxybutyl]pyridinium tetraphenylborate;

N-(2-benzoyloxyethyl)pyridinium tetraphenylborate;

N-(2-benzoyloxyethyl)pyridinium bromide, and

N-(2-acetyloxyethyl)pyridinium bromide.

Presently preferred salts are estercontaining quaternary pyridinium salts of the invention wherein in the formula set forth above $R_1$ is phenyl or methyl, n is 2, $Z^\ominus$ is m-nitrobenzenesulfonate or tetraphenylborate and Y is hydrogen.

(C) Synthesis

The salts of the present invention can be prepared by any convenient route. One general route is to quaternize a pyridine compound with an acyloxyalkylhalide. The quaternary pyridinium halide can then be reacted with an alkali metal arylsulfonate or other acid salt through ion exchange to give the desired N-(acyloxyalkyl)-pyridinium salt.

One convenient and presently preferred procedure for the preparation of the quaternary pyridinium salt is to prepare the acyloxyalkylhalide and the pyridine compound as solutes in the same highly polar solvent, acetonitrile being one presently particularly preferred example. The mole ratio of pyridine compound to the quaternizing agent is preferably about 1:1. Such a solution is then heated at reflux for a time in the range of from about 15 to about 20 hours. The reaction mixture is then cooled or concentrated by solvent evaporation to yield an oil or a crystalline solid. The product can be used without further purification for the next step in the synthesis, or the product can be purified by recrystallization, for example, from a ketone, such as 2-butanone, or the like, followed by washing and drying.

One convenient and presently preferred procedure for preparation of the quaternary pyridinium organic salt from the intermediate halide is to dissolve the ion exchange agent in water and add this solution to a second aqueous solution containing the quaternary pyridinium salt intermediate. The mole ratio of such salt to such ion exchange agent should be about 1:1. Typically, a precipitate is formed immediately. The resulting product can be recrystallized from acetonitrile or ethyl acetate or any other suitable recrystallizing solvent.

(D) Toners and Toner Preparation

The quaternary pyridinium salts of the present invention are incorporated into toner particles. For present purposes, toner particles can be regarded as being preferably comprised on a 100 weight percent basis of:
(a) about 0.5 to about 10 weight percent of at least one quaternary pyridinium salt;
(b) about 75 to about 97.5 weight percent of a thermoplastic polymer; and
(c) about 2 to about 15 weight percent of a colorant.

The size of the toner particles is believed to be relatively unimportant from the standpoint of the present invention; rather the exact size and size distribution is influenced by the end use application intended. So far as now known, the toner particles can be used in all known electrostatographic copying processes. Typically and illustratively, toner particle sizes range from about 0.5 to about 100 microns, preferably from about 4 to about 35 microns.

The properties of the thermoplastic polymers employed as the toner matrix phase materials with the salts of the present invention can vary widely. Typically, and preferably, amorphous toner polymers having a glass transition temperature in the range of about 50° to about 129° C. or blends of substantially amorphous polymers with substantially crystalline polymers having a melting temperature in the range of about 65° to about 200° C. are utilized in the present invention. Preferably, such polymers have a number average molecular weight in the range of about 1,000 to about 500,000. The weight average molecular weight can vary, but preferably is in the range of about $2 \times 10^3$ to about $10^6$. Typical examples of such polymers include polystyrene, polyacrylates, polyesters, polyamides, polyolefins, polycarbonates, phenol formaldehyde condensates, alkyl resins, polyvinylidene chlorides, epoxy resins, various copolymers of the monomers used to make these polymers, such as polyesteramides, acrylonitrile copolymers with monomers, such as styrene, acrylics, and the like.

Preferably, the thermoplastic polymers used with the salts of this invention are substantially amorphous. However, as indicated above, mixtures of polymers can be employed, if desired, such as mixtures of substantially amorphous polymers with substantially crystalline polymers.

Presently preferred polymers for use in toner powders are styrene/n-butyl acrylate copolymers. In general, preferred styrene/n-butyl acrylate copolymers have a glass transition temperature (Tg) in the range of about 50° to about 100° C.

An optional but preferred starting material for inclusion in such a blend is a colorant (pigment or dye). Suitable dyes and pigments are disclosed, for example, in U.S. Reissue Pat. No. 31,072, and in U.S. Pat. Nos. 4,140,644; 4,416,965; 4,414,152; and 2,229,513. One particularly useful colorant for the toners to be used in black and white electrophotographic copying machines is carbon black. When employed, colorants are generally employed in quantities in the range of about 1 to about 30 weight percent on a total toner powder weight basis, and preferably in the range of about 2 to about 15 weight percent.

Toner compositions, if desired, can also contain other additives of the types which have been heretofore employed in toner powders, including leveling agents, surfactants, stabilizers, and the like. The total quantity of such additives can vary. A present preference is to employ not more than about 10 weight percent of such additives on a total toner powder composition weight basis.

Various procedures are known to the art for incorporating additives, such as the quaternary pyridinium salts of the present invention, colorants, or the like, into a desired polymer or mixture of polymers. For example, a preformed mechanical blend of particulate polymer particles, quaternary pyridinium salts, colorants, etc., can be roll milled or extruded at a temperature sufficient to melt blend the polymer, or mixture of polymers, to achieve a uniformly blended composition. Thereafter, the cooled composition can be ground and classified, if desired, to achieve a desired toner powder size and size distribution.

Preferably, prior to melt blending, the toner components, which preferably are preliminarily placed in a particulate form, are blended together mechanically. With a polymer having a Tg in the range of about 50° to 120° C. or a Tm in the range of about 65° to about 200° C., a melt blending temperature in the range of about 90° to about 240° C. is suitable using a roll mill or extruder. Melt blending times (that is, the exposure period for melt blending at elevated temperatures) are in the range of about 1 to about 60 minutes. After melt blending and cooling, the composition can be stored before being ground. Grinding can be carried out by any convenient procedure. For example, the solid composition can be crushed and then ground using, for example, a fluid energy or jet mill, such as described in U.S. Pat. No. 4,089,472. Classification, if employed, can be conventionally accomplished using one or two steps.

In place of melt blending, the polymer can be dissolved in a solvent and the additives dissolved and/or dispersed therein. Thereafter, the resulting solution or dispersion can be spray dried to produce particulate toner powders.

Limited coalescence polymer suspension procedures are particularly useful for producing small sized, uniform toner particles, such as toner particles under about 10 microns in size.

The toner powders used with the salts of the present invention preferably have a fusing temperature latitude in the range of about 275° to about 400° F., although toner powders with higher and lower fusing temperatures can be prepared and used. The toner powders characteristically display excellent paper adhesion characteristics. Typically, the toner powders have a paper adhesion index value in the range of about 30 to about 100, although toner powders with lower such values can be prepared and used. Paper adhesion index values of such toner powders are characteristically higher than those of toner powders prepared with the same polymer and additives but containing a quaternary ammonium salt not of this invention and are comparable to or higher than a toner powder prepared with the same polymer and additives but containing no charge control agent.

To be utilized as toners in electrostatographic developers, toners containing the novel salts of this invention can be mixed with a carrier vehicle. The carrier vehicles which can be used to form such developer compositions can be selected from a variety of materials. Such materials include carrier core particles and core particles overcoated with a thin layer of film-forming resin.

The carrier core materials can comprise conductive, non-conductive, magnetic, or non-magnetic materials. For example, carrier cores can comprise glass beads; crystals of inorganic slats such as aluminum potassium chloride; other salts such as ammonium chloride or sodium nitrate; granular zircon; granular silicon; silicon dioxide; hard resin particles such as poly(methyl methacrylate); metallic materials such as iron, steel, nickel, carborundum, cobalt, oxidized iron; or mixtures or alloys of any of the foregoing. See, for example, U.S. Pat. Nos. 3,850,663 and 3,970,571. Especially useful in magnetic brush development schemes are iron particles such as porous iron particles having oxidized surfaces, steel particles, and other "hard" or "soft" ferromagnetic materials such as gamma ferric oxides or ferrites, such as ferrites of barium, strontium, lead, magnesium, or aluminum. See for example, U.S. Pat. Nos. 4,042,518; 4,478,925; and 4,546,060.

As noted above, the carrier particles can be overcoated with a thin layer of a film-forming resin for the purpose of establishing the correct triboelectric relationship and charge level with the toner employed. Examples of suitable resins are the polymers described in U.S. Pat. Nos. 3,547,822; 3,632,512; 3,795,618 and 3,898,170 and Belgian Patent No., 797,132. Other useful resins are fluorocarbons such as polytetrafluoroethylene, poly(vinylidene fluoride), mixtures of these, and copolymers of vinylidene fluoride and tetrafluoroethylene. See, for example, U.S. Pat. Nos. 4,545,060; 4,478,925; 4,076,857; and 3,970,571. Such polymeric fluorohydrocarbon carrier coatings can serve a number of known purposes. One such purposes can be to aid the developer to meet the electrostatic force requirements mentioned above by shifting the carrier particles to a position in the triboelectric series different from that of the uncoated carrier core material, in order to adjust the degree of triboelectric charging of both the carrier and toner particles. Another purpose can be to reduce the frictional characteristics of the carrier particles in order to improve developer flow properties. Still another purpose can be to reduce the surface hardness of the carrier particles so that they are less likely to break apart during use and less likely to abrade surfaces (e.g., photoconductive element surfaces) that they contact during use. Yet another purpose can be to reduce the tendency of toner material or other developer additives to become undesirably permanently adhered to carrier surfaces during developer use (often referred to as scumming). A further purpose can be to alter the electrical resistance of the carrier particles.

A typical developer composition containing the above-described toner and a carrier vehicle generally comprises from about 1 to about 20 percent by weight of particulate toner particles and from about 80 to about 99 percent by weight carrier particles. Usually, the carrier particles are larger than the toner particles. Conventional carrier particles have a particle size on the order of from about 20 to about 1200 microns, preferably 30–300 microns.

Alternatively, toners containing salts of the present invention can be used in a single component developer, i.e., with no carrier particles.

Toner and developer compositions containing salts of this invention can be used in a variety of ways to develop electrostatic charge patterns or latent images. Such developable charge patterns can be prepared by a number of means and be carried for example, on a light sensitive photoconductive element or a non-light-sensitive dielectric-surface element such as an insulator-coated conductive sheet. One suitable development technique involves cascading the developer composition across the electrostatic charge pattern, while another technique involves applying toner particles from a magnetic brush. This latter technique involves the use of a magnetically attractable carrier vehicle in forming the developer composition. After imagewise deposition of the toner particles, the image can be fixed, e.g., by heating the toner to cause it to fuse to the substrate carrying the toner. If desired, the unfused image can be transferred to a receiver such as a blank sheet of copy paper and then fused to form a permanent image.

The invention is further illustrated by the following Examples. In these Examples, all melting points and boiling points are uncorrected. NMR (nuclear magnetic resonance) spectra were obtained with a Varian Gemini-200 NMR spectrometer. All elemental analyses were performed by combustion. Unless otherwise indicated, all starting chemicals were commercially obtained.

EXAMPLES

Example 1: Preparation of 2-Bromoethyl Benzoate

A mixture of 120.14 grams (0.80 mol) of 2-phenyl-1,3-dioxolane, 142.39 grams (0.80 mol) of N-bromosuccinimide, 1 liter of carbon tetrachloride and a catalytic amount of benzoyl peroxide was heated with stirring at reflux for 5.25 hours and then cooled. The mixture was filtered, and the filtrate was concentrated to an oil. Distillation of this oil gave 147.8 grams; (80.65% of theory) of the product; bp=104°-111° C./0.40 mm.

Anal. Calcd. for $C_9H_9BrO_2$: C, 47.19; H, 3.96; Found: C, 46.89; H, 4.24;

NMR agreed With the proposed structure.

Example 2: Preparation of N-(2-Benzoyloxyethyl)-pyridinium Bromide

A solution of 50.0 grams (0.218 mol) of 2-bromoethyl benzoate, 17.27 grams (0.218 mol) of pyridine and 135 milliliters of acetonitrile was heated at reflux for 17.75 hours and cooled. Solid crystallized and was collected, washed with acetonitrile, then with ether and dried. The yield of product was 48.5 grams (72.19% of theory); mp=162°-164° C.

Anal. Calcd for $C_{14}H_{14}BrNO_2$: C, 54.56; H, 4.58; N, 4.55; Found: C, 54.33; H, 4.59; N, 4.51.

NMR agreed with the proposed structure.

Example 3: Preparation of N-(2-Benzoyloxyethyl)-pyridinium Tetraphenylborate A solution of 17.11 grams (0.05 mol) of sodium tetraphenylborate in 50 milliliters of water was added to a solution of 15.41 grams (0.05 mol) of N-(2-benzoyloxyethyl)pyridinium bromide prepared as described in Example 2, in 50 milliliters of water. An additional 200 milliliters of water was added and the mixture was stirred and allowed to stand for 1 hr. The mixture was diluted with more water and filtered. The solid collected was washed with water and dried. Recrystallization from acetonitrile gave 15.5 grams (56.62% of theory) of product; mp=135°-138° C.

Anal. Calcd. for $C_{38}H_{34}BNO_2$: C, 83.36; H, 6.26; B, 1.97; N, 2.56; Found: C, 83.09; H, 6.32; B, 2.05; N, 2.55.

NMR agreed With the proposed structure.

Example 4: Preparation of N-(2-Benzoyloxyethyl)-pyridinium m-Nitrobenzenesulfonate A solution of 11.26 grams (0.05 mol) of sodium m-nitrobenzenesulfonate in 50 milliliters of water was added to a solution of 15.41 grams (0.05 mole) of N-(2-benzoyloxyethyl)pyridinium bromide, prepared as described in Example 2, in 50 milliliters of water. The resultant solution was treated with methylene chloride resulting in the formation of three layers. The center layer was isolated, treated with ligroine (bp=70°-90° C.) and allowed to stand with spatula scratching of the oil. Crystallization occurred and the solid was collected, washed with ether and recrystallized from acetonitrile. The yield of product was 6.6 grams (30.67% of theory); mp=128°-30° C.

Anal. Calcd. $C_{20}H_{18}N_2O_7S$: C, 55.81; H, 4.22; N, 6.51; S, 7.45; Found: C, 55.33; H, 4.24; N, 6.52; S, 7.65.

NMR agreed With the proposed structure.

Example 5: Preparation of N-(2-Acetyloxyethyl)-pyridinium Bromide

A solution of 100.0 grams (0.599 mol) of 2-bromoethyl acetate, 47.37 grams (0.599 mol) of pyridine and 300 milliliters of acetonitrile was heated at reflux for 19 hours and then cooled, concentrated on a rotovap to an oil, heated in methyl ethyl ketone and then cooled. On prolonged standing, solid crystallized was collected and dried. The yield of product was 129.5 grams (87.85% of theory); mp=69°-74° C.

Anal. Calcd. for $C_9H_{12}BrNO_2$: C, 43.92; H, 4.91; N, 5.69; Found: C, 43.33; H, 4.83; N, 5.67.

NMR agreed With the proposed structure.

Example 6: Preparation of N-(2-Acetyloxyethyl)-pyridinium Tetraphenylborate

To a solution of 24.61 grams (0.10 mol) of N-(2-acetyloxyethyl)pyridinium bromide in 250 milliliters of water there was added a solution of 34.24 grams (0.10 mol) of sodium tetraphenylborate in 150 milliliters of water. An oily precipitate formed which was treated with 500 milliliters of water to give a white solid. The solid was collected and recrystallized from acetonitrile. The yield of product was 39.8 grams (81.99 % of theory); mp=223°-224° C.

Anal. Calcd. for $C_{33}H_{32}BNO_2$: C, 81.65; H, 6.64; B, 2.23; N, 2.89; Found: C, 81.32; H, 6.75; B, 2.11; N, 2.89.

NMR agreed With the proposed structure.

Examples 7: Toner Powder Preparation (Dry Weight Basis)

A styrene/n-butyl acrylate copolymer was obtained by limited coalescence polymerization and blended with the additive components as identified in the following Table I in the amounts set forth therein.

TABLE I

| Component | Blend A pph[1] | Blend B pph[1] | Blend C pph[1] | Blend D pph[1] | Blend E pph[1] |
|---|---|---|---|---|---|
| Styrene/n-butyl acrylate | 100 | 100 | 100 | 100 | 100 |
| Carbon black | 6 | 6 | 6 | 6 | 6 |
| Charge control agent: | | | | | |
| None | | | | | |
| N-(2-benzoyloxyethyl)pyridinium tetraphenylborate | 0 | 1 | 0 | 0 | 0 |

TABLE I-continued

| Component | Blend A pph[1] | Blend B pph[1] | Blend C pph[1] | Blend D pph[1] | Blend E pph[1] |
|---|---|---|---|---|---|
| (formulation of Example 3) | | | | | |
| N-(2-benzoyloxy-ethyl)pyridinium m-nitrobenzene-sulfonate (formulation of Example 4) | 0 | 0 | 1 | 0 | 0 |
| N-(2-acetyloxy-ethyl)pyridinium tetraphenylborate (formulation of Example 6) | 0 | 0 | 0 | 1 | 0 |
| N-octadecyl-N,N-dimethyl-benzylammonium m-nitrobenzene-sulfonate | 0 | 0 | 0 | 0 | 1 |

[1]Parts by Weight

The carbon black was "Regal TM 300". Each blend was roll milled at 150° C. for 20 minutes, cooled, crushed and classified to produce a toner powder product having a size of about 12 microns and a size distribution of about 2-30 microns. The charge control agent identified in Table I above as N-octadecyl-N,N-dimethylbenzylammonium m-nitrobenzenesulfonate was utilized for comparative purposes.

Example 8: Fusing And Adhesion Performance

Each of the styrene/n-butyl acrylate toner powder Blends A, B, C, D and E was evaluated on a fusing breadboard consisting of a fusing roller coated with 100 mils of red rubber, engaged at constant speed and pressure onto a backup roller coated with polytetrafluoroethylene (available commercially as Silverstone TM from E.I. duPont de Nemours and Co.) Both roller surfaces were coated by hand with a release oil (60,000 centistoke polydimethylsiloxane oil available from Dow Corning Co.). The nip width between the two rollers was 0.215-0.240 inch and the fuser was operated at 12 inches/second. The fusing temperature was 350° F.

Six longitudinally extending stripes of toner were applied to the wire side of Kodak alkaline DP paper, and the toned papers were run through the fusing breadboard. The transmission density of the toned, fused stripes was between 1.2 and 1.5.

The adhesion index was determined for each stripe, and the results for each of the various toner Blends A, B, C, D and E are presented in Table II below.

TABLE II

| Blend | Charge Control Agent | Average Adhesion Index (AI) of Toner |
|---|---|---|
| A | none | 69 |
| B | N-(2-benzoyloxyethyl)-pyridinium tetraphenylborate (formulation of Example 3) | 79 |
| C | N-(2-benzoyloxyethyl)-pyridinium m-nitrobenzene-sulfonate (formulation of Example 4) | 94 |
| D | N-(2-acetyloxyethyl)-pyridinium tetraphenyl-borate (formulation of Example 6) | 66 |
| E | N-octadecyl-N,N-dimethyl-benzylammonium m-nitro-benzenesulfonate | 37 |

The adhesion index values are the average of 8 measurements and the standard deviations are less than 7 units for the measurements. The toners containing the ester-containing quaternary pyridinium salts of the invention (Blends B, C and D) had significantly higher adhesion indexes than the toner containing the N-octadecyl-N,N-dimethylbenzylammonium m-nitrobenzenesulfonate charge control agent, the comparative charge control agent outside the scope of the invention, and had comparable or significantly higher adhesion indexes than the toner without a charge control agent.

This invention has been described in detail with particular reference to preferred embodiments thereof, but it will be understood that variations and modifications can be effected within the spirit and scope of the invention.

We claim:

1. An ester-containing quaternary pyridinium salt useful in electrostatographic toners as a charge control agent having the structure:

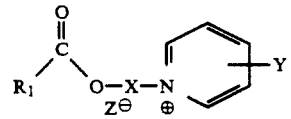

wherein $R_1$ is alkyl, phenyl, naphthyl or anthryl, X is $+CH_2+_n$, Y is hydrogen, alkyl, alkoxy or halogen, $Z^\ominus$ is an anion selected from the group consisting of tosylate, tetraphenylborate and m-nitrobenzenesulfonate and n is an integer from 2 to 6.

2. The salt of claim 1, wherein said salt is N-[2-benzoyloxyethyl]pyridinium m-nitrobenzenesulfonate.

3. The salt of claim 1, wherein said salt is N-[2-(4-chlorobenzoyloxy)ethyl]pyridinium m-nitrobenzenesulfonate.

4. The salt of claim 1, wherein said salt is N-[3-(3-nitrobenzoyloxy)propyl]pyridinium tetraphenyl-borate.

5. The salt of claim 1, wherein said salt is N-[2-(2-naphthoyloxy)ethyl]pyridinium tetraphenyl-borate.

6. The salt of claim 1, wherein said salt is N-[2-acetyloxyethyl]pyridinium tetraphenylborate.

7. The salt of claim 1, wherein said salt is 2-acetyloxyethyl]pyridinium m-nitrobenzenesulfonate.

8. The salt of claim 1, wherein said salt is N-[4-propionyloxybutyl]pyridinium tetraphenylborate.

9. The salt of claim 1, wherein said salt is N-(2-benzoyloxyethyl)pyridinium tetraphenylborate.

* * * * *

UNITED STATES PATENT AND TRADEMARK OFFICE
CERTIFICATE OF CORRECTION

PATENT NO. : 5,196,539

DATED : March 23, 1993

INVENTOR(S) : John C. Wilson and Alexandra D. Bermel

It is certified that error appears in the above-indentified patent and that said Letters Patent is hereby corrected as shown below:

On the title page, Item [75] Inventor should read —John C. Wilson—.

Signed and Sealed this

Twenty-third Day of August, 1994

Attest:

BRUCE LEHMAN

*Attesting Officer*  *Commissioner of Patents and Trademarks*